(12) United States Patent
Fontanez et al.

(10) Patent No.: US 11,827,936 B2
(45) Date of Patent: Nov. 28, 2023

(54) METHODS AND SYSTEMS FOR SINGLE CELL GENE PROFILING

(71) Applicant: Fluent Biosciences Inc., Watertown, MA (US)

(72) Inventors: Kristina Fontanez, Arlington, MA (US); Robert Meltzer, Belmont, MA (US); Yi Xue, Shrewsbury, MA (US); Christopher D'amato, Wellesley, MA (US); Sepehr Kiani, Watertown, MA (US)

(73) Assignee: Fluent Biosciences Inc., Watertown, MA (US)

( * ) Notice: Subject to any disclaimer, the term of this patent is extended or adjusted under 35 U.S.C. 154(b) by 0 days.

(21) Appl. No.: 17/146,720

(22) Filed: Jan. 12, 2021

(65) Prior Publication Data

US 2021/0214792 A1 Jul. 15, 2021

Related U.S. Application Data

(60) Provisional application No. 62/960,404, filed on Jan. 13, 2020.

(51) Int. Cl.
*C12Q 1/68* (2018.01)
*C12Q 1/6876* (2018.01)
*C12Q 1/686* (2018.01)
*C12N 15/10* (2006.01)

(52) U.S. Cl.
CPC ....... *C12Q 1/6876* (2013.01); *C12N 15/1096* (2013.01); *C12Q 1/686* (2013.01)

(58) Field of Classification Search
None
See application file for complete search history.

(56) References Cited

U.S. PATENT DOCUMENTS

| | | | |
|---|---|---|---|
| 7,537,897 | B2 | 5/2009 | Brenner et al. |
| 7,842,457 | B2 | 11/2010 | Berka et al. |
| 3,012,690 | A1 | 9/2011 | Berka et al. |
| 8,715,934 | B2 | 5/2014 | Diehl et al. |

(Continued)

FOREIGN PATENT DOCUMENTS

| | | |
|---|---|---|
| AU | 2013203624 A1 | 5/2013 |
| WO | 2010/117620 A2 | 10/2010 |

(Continued)

OTHER PUBLICATIONS

Salomon et al. (Lab Chip, 2019, vol. 19, p. 1706-1727) (Year: 2019).*

(Continued)

*Primary Examiner* — Stephanie K Mummert
(74) *Attorney, Agent, or Firm* — Withers Bergman, LLP; Thomas C. Meyers

(57) ABSTRACT

This disclosure provides methods and systems for single-cell analysis, including single-cell transcriptome analysis, of target cells without microfluidic devices. The disclosed methods involve the use of template particles to template the formation of monodisperse droplets to generally capture a single target cell from a population of cells in an encapsulation, derive a plurality of distinct mRNA molecules from the single target cell, and quantify the distinct mRNA molecules to generate an expression profile.

17 Claims, 5 Drawing Sheets

(56) References Cited

U.S. PATENT DOCUMENTS

| | | | |
|---|---|---|---|
| 8,748,102 B2 | 6/2014 | Berka et al. | |
| 8,765,380 B2 | 7/2014 | Berka et al. | |
| 9,011,777 B2 | 4/2015 | Beer | |
| 9,012,390 B2 | 4/2015 | Holtze et al. | |
| 9,085,798 B2 | 7/2015 | Chee | |
| 9,260,751 B2 | 2/2016 | Diehl et al. | |
| 9,388,465 B2 | 7/2016 | Hindson et al. | |
| 9,562,837 B2 | 2/2017 | Link | |
| 9,567,645 B2 | 2/2017 | Fan et al. | |
| 9,567,646 B2 | 2/2017 | Fan et al. | |
| 9,580,736 B2 | 2/2017 | Tan et al. | |
| 9,598,736 B2 | 3/2017 | Fan et al. | |
| 9,637,799 B2 | 5/2017 | Fan et al. | |
| 9,650,629 B2 | 5/2017 | Froehlich et al. | |
| 9,701,998 B2 | 7/2017 | Tindson et al. | |
| 9,708,654 B2 | 7/2017 | Hunicke-Smith et al. | |
| 9,783,847 B2 | 10/2017 | Chee | |
| 9,951,386 B2 | 4/2018 | Hindson et al. | |
| 10,030,267 B2 | 7/2018 | Hindson et al. | |
| 10,041,116 B2 | 8/2018 | Hindson et al. | |
| 10,131,958 B1 | 11/2018 | Fan et al. | |
| 10,151,003 B2 | 12/2018 | Fan et al. | |
| 10,155,981 B2 | 12/2018 | Brenner et al. | |
| 10,202,628 B2 | 2/2019 | Church et al. | |
| 10,208,356 B1 | 2/2019 | Fan et al. | |
| 10,221,442 B2 | 3/2019 | Hindson et al. | |
| 10,240,192 B2 | 3/2019 | Berka et al. | |
| 10,240,197 B1 | 3/2019 | Brenner et al. | |
| 10,253,375 B1 | 4/2019 | Fan et al. | |
| 10,266,883 B2 | 4/2019 | Chee | |
| 10,280,459 B1 | 5/2019 | Brenner et al. | |
| 10,285,940 B2 | 5/2019 | Mason et al. | |
| 10,329,557 B2 | 6/2019 | Johnson et al. | |
| 10,344,329 B2 | 7/2019 | Hindson et al. | |
| 10,392,662 B1 | 8/2019 | Brenner et al. | |
| 10,400,280 B2 | 9/2019 | Tindson et al. | |
| 10,415,030 B2 | 9/2019 | Marshall et al. | |
| 10,457,986 B2 | 10/2019 | Hindson et al. | |
| 10,501,793 B2 | 12/2019 | Chee | |
| 10,584,381 B2 | 3/2020 | Hindson et al. | |
| 2003/0180737 A1 | 9/2003 | Gu et al. | |
| 2009/0280475 A1 | 11/2009 | Pollack et al. | |
| 2011/0086780 A1 | 4/2011 | Colston, Jr. et al. | |
| 2011/0118151 A1 | 5/2011 | Shoo et al. | |
| 2011/0311978 A1 | 12/2011 | Makarewicz, Jr. et al. | |
| 2012/0316074 A1 | 12/2012 | Saxonov | |
| 2013/0115169 A1 | 5/2013 | Lahann et al. | |
| 2014/0155295 A1* | 6/2014 | Hindson | B01L 3/523 506/30 |
| 2015/0225777 A1 | 8/2015 | Hindson et al. | |
| 2017/0192030 A1 | 7/2017 | Lapham et al. | |
| 2017/0218437 A1 | 8/2017 | Seul et al. | |
| 2017/0255160 A1 | 9/2017 | Numata et al. | |
| 2018/0010105 A1 | 1/2018 | Rogers et al. | |
| 2018/0133715 A1 | 5/2018 | Craig et al. | |
| 2018/0216162 A1 | 8/2018 | Belhocine et al. | |
| 2018/0237836 A1 | 8/2018 | Abate et al. | |
| 2018/0274027 A1 | 9/2018 | Hindson et al. | |
| 2019/0153532 A1* | 5/2019 | Bharadwaj | C12N 15/1065 |
| 2019/0177789 A1 | 6/2019 | Hindson et al. | |
| 2019/0323091 A1 | 10/2019 | Bramlett et al. | |
| 2019/0382753 A1 | 12/2019 | Steemers et al. | |
| 2020/0261879 A1 | 8/2020 | Abate et al. | |

FOREIGN PATENT DOCUMENTS

| | | | |
|---|---|---|---|
| WO | 2011/047307 A1 | 4/2011 | |
| WO | 2014/028537 A1 | 2/2014 | |
| WO | 2014/153071 A1 | 9/2014 | |
| WO | 2015/157369 A1 | 10/2015 | |
| WO | 2015/187792 A1 | 12/2015 | |
| WO | 2016/025815 A1 | 2/2016 | |
| WO | 2016/040476 A1 | 3/2016 | |
| WO | 2016/126871 A2 | 8/2016 | |
| WO | 2016/138080 A1 | 9/2016 | |
| WO | 2017/161306 A1 | 9/2017 | |
| WO | 2019/011971 A1 | 1/2019 | |
| WO | 2019/023627 A1 | 1/2019 | |
| WO | 2019/139650 A2 | 7/2019 | |
| WO | 2019/157529 A1 | 8/2019 | |
| WO | 2019/204229 A1 | 10/2019 | |
| WO | 2019/217552 A1 | 11/2019 | |
| WO | WO-2020037214 A1 * | 2/2020 | ............ B01J 13/003 |
| WO | 2020/069268 A1 | 4/2020 | |
| WO | 2020/069298 A1 | 4/2020 | |

OTHER PUBLICATIONS

Mimitou et al. (Nature Methods, 2019, vol. 19, 409-412) (Year: 2019).*

Hatori, 2019, Particle-Templated Emulsification for Microfluidics-Free Digital Biology, Analytical Chemistry, 90:9813-9820.

International Search Report and Written Opinion issued in International Application No. PCT/US2020/47214, dated Feb. 2, 2021, 14 pages.

International Search Report and Written Opinion issued in International Application No. PCT/US2021/013042, dated Mar. 29, 2021, 9 pages.

International Search Report and Written Opinion issued in International Application No. PCT/US2021/013045, dated Mar. 29, 2021, 8 pages.

International Search Report and Written Opinion issued in International Application No. PCT/US2021/013065, dated Mar. 29, 2021, 11 pages.

International Search Report and Written Opinion issued in International Application No. PCT/US2021/013066, dated Mar. 29, 2021, 11 pages.

International Search Report and Written Opinion issued in International Application No. PCT/US2021/13048, dated Mar. 31, 2021, 20 pages.

International Search Report and Written Opinion issued in International Application No. PCT/US2021/13069, dated Apr. 1, 2021, 14 pages.

Kumari, 2017, Quantification of Circulating Free DNA as a Diagnostic Marker in Gall Bladder Cancer, Pathology & Oncology Research, 23:91-97.

Mazutis, 2013, Singl-cell analysis and sorting using droplet-based microfluidics, Nature Protocols, 8(5):870-891.

Non-Final Office Action issued in U.S. Appl. No. 17/146,986, dated Mar. 11, 2021, 7 pages.

Strachan, Human Molecular Genetics 2 (Wiley-Liss, New York, 1999).

Vitale, 2019, An Optimized Workflow to Evaluate Estrogen Receptor Gene Mutations in Small Amounts of Cell-Fee DNA, The Journal of Molecular Diagnostics, 21(1):123-127.

Bowman, 2013, Multiplexed Illumina sequencing libraries from picogram quantities of DNA, BMC Genomics 14:466 (8 pages).

Eastburn, 2013, Ultrahigh-trhoughput mammalian single-cell reverse-transcriptase polymerase chain reaction in microfluidic drops, Anal Chem 85:8016-8021.

Figueiredo, 2007, Cost effective method for construction of high quality cDNA libraries, Biomol Eng 24:419-421.

Fu, 2015, Uniform and accurate single-cell sequencing based on emulsion whole-genome amplification, PNAS 112(38):11923-11928.

Kumaresan, 2008, High-throughput single copy DNA amplification and cell analysis in engineered nanoliter droplets, Anal Chem, 80:3522-3529.

Lage, 2003, Whole genome analysis of genetic alterations in small DNA samples using hyperbranched strand displacement amplification and array-CGH, Genome Res 13:294-307.

Lyons, 2017, Large-scale DNA barcode library generation for biomolecule identification in high-throughput screens, Sci Rep 7:13899 (7 pages).

Nishikawa, 2015, Monodisperse picoliter droplets for low-bias and contamination-free reactions in single-cell whole genome amplification, PLoSOne 10(9):e0138733 (15 pages).

(56) References Cited

OTHER PUBLICATIONS

Roche, 2011, emPCR amplificaiotn method manual, 454 Life Sciences Corp (12 pages).
Sidore, 2016, Enhanced sequencing coverage with digital droplet multiple displacement amplification, Nucl Acids Res 44(7):e66 (9 pages).
Stoeckius, 2017, Simultaneous epitope and transcriptome measurment in single cells, Nat Meth online pub (10 pages).
Tamminen, 2015, Single gene-based distinction of individual microbial genomes from a mixed population of microbial cells Front Microb 6:195 (10 pages).
Zilionis, 2016, Single-cell barcoding and sequencing using droplet microfluidics, Natutre Prot 12(1):44-73.
Int Search Report and Written Op dated Jun. 30, 2021, for Int Application No. PCT/US2021/023815, filed Mar. 24, 2021 (14 pages).
Walls, 2020, Structure, Function, and Antigenicity of the SARS-CoV-2 Spike Glcoprotein, Cell, 181(2):281-292.
Int Search Report and Written OP dated Aug. 11, 2021, for Int Application No. PCT/US2021/022503, filed Mar. 16, 2021 (9 pages).

\* cited by examiner

METHODS AND SYSTEMS FOR SINGLE CELL GENE PROFILING

TECHNICAL FIELD

This disclosure relates to methods and systems for single cell gene profiling.

BACKGROUND

The complexity of biological systems necessitates many experiments to characterize them. High-throughput methods are often implemented to reduce the number of individual experiments that need to be performed. Unfortunately, methods for high-throughput analysis of single cells are constrained by costs associated with isolating single cells and preparing libraries.

Methods for isolating single cells generally require microfluidic devices that are complicated to use and expensive to operate. Moreover, since cells are processed individually, microfluidic devices are inherently limited in terms of the number of cells that can be assayed in a given experiment. And as such, high-throughput single cell systems are unavailable in many clinical and research facilities.

SUMMARY

This disclosure provides methods and systems for single-cell analysis, including single-cell transcriptome analysis, of target cells without microfluidic devices. Methods and systems of the invention generate an emulsion with template particles to segregate individual target cells into monodisperse droplets. Nucleic acid molecules are released from the target cells inside the monodisperse droplets and are quantified to generate expression profiles for each of the target cells. This approach provides a massively parallel analytical workflow that is inexpensive and scalable to ascertain expression profiles of millions of single cells with a single library preparation.

Methods and systems of the invention use template particles to template the formation of monodisperse droplets and isolate target cells for gene profiling. Methods include combining template particles with target cells in a first fluid, adding a second fluid to the first fluid, shearing the fluids to generate a plurality of monodisperse droplets simultaneously wherein each of the monodisperse droplets contain a single one of the template particles and a single one of the target cells. Methods further include lysing the target cells within the monodisperse droplets to release a plurality of distinct mRNA molecules and quantifying the plurality of distinct mRNA molecules. Data generated by quantifying the mRNA is used to create expression for each of the target cells. Methods further include processing the expression profiles to identify characteristics of the target cells that can be used to, for example, make a diagnosis, prognosis, or determine drug effectiveness.

Methods and systems of the invention provide a method for quantifying gene expression of target cells. The method includes releasing mRNA from target cells inside monodisperse droplets. The mRNA may be reverse transcribed into cDNA and simultaneously barcoded. The barcoded cDNA is amplified to generate a plurality of barcoded amplicons. The amplicons can be sequenced by next generation sequencing methods, and because of the barcodes, each sequence read can be traced back to the target cell. The sequence reads are processed by certain computer algorithms to generate an expression profile for the target cell.

After obtaining expression profiles from target cells, the profiles may be analyzed by comparing the profiles with reference or control profiles to ascertain information about the target cells. In other instances, profiles of target cells can be compared to profiles derived from cells with certain phenotypes to determine whether the target cells share characteristics of the cells of the phenotype.

In one aspect, methods and systems of the invention provide a method for identifying the presence of a rare cell in a heterogeneous cell population. The method includes isolating a plurality of target cells by combining target cells with a plurality of template particles in a first fluid, adding a second fluid that is immiscible with the first fluid, and shearing the fluids to generate an emulsion comprising monodisperse droplets that contain a target cell and a single template particle. Methods further include releasing a plurality of mRNA molecules inside the droplet containing the target cell and quantifying the plurality of mRNA molecules. Quantifying may include reverse transcribing the mRNA into cDNA that is barcoded. The barcoded cDNA may be amplified to generate a plurality of barcoded amplicons that can be traced back to the target cell. In some instances, methods may include sequencing the plurality of barcoded amplicons by, for example, next-generation sequencing methods to generate sequence reads. Methods may further include processing the sequence reads to generate expression profiles for each target cell and using the data by, for example, performing a gene clustering analysis to identify one or more cell types or cell states among the target cells.

In another aspect, methods and systems of the disclosure provide a method for analyzing a heterogeneous tumor biopsy taken from a subject. The method includes obtaining a biopsy from a patient and isolating a population of cells from the biopsy. The method further includes segregating the population of cells into droplets by creating a mixture of the population of cells and a plurality of template particles an aqueous fluid, adding an oil, and vortexing the mixture to generate an emulsion comprising droplets that each contain a single one of the population of cells and a template particle. Methods further include releasing mRNA from each one of the cells inside droplets and performing transcriptome analysis on one or more genes. The analysis of one or more genes may be used to identify one or more characteristics of a cancer. A characteristic of cancer can be the presence, or absence, of one or more gene transcripts associated with cancer. A method disclosed herein can further comprise the step of using the characteristic to diagnose the subject with cancer and devise a treatment plan.

In some aspects, methods and systems of the invention provide a method for determining the potential effectiveness of a therapeutic agent. The method comprises segregating a first population of diseased cells into droplets with template particles and determining gene expression from at least one of the diseased cells, thereby producing a disease-state expression signature. The method further includes exposing a second population of disease state cells to an agent and determining gene expression of second population of cells and comparing the gene expression with the disease-state expression signature to ascertain the effectiveness of the agent against the disease based on an elevated or repressed level of expression of one or more genes. In some embodiments, the therapeutic agent may be delivered to second population of cells inside the droplets. For example, the agent may be associated with the template particle by tethering the agent to an external surface of the template particle, or packaging the agent inside a compartment of the template particle and releasing the agent from the template particle inside the droplets.

In certain aspects, the methods and systems of the invention provide a method for segregating cells into droplets. The droplets may be prepared as emulsions, e.g., as an aqueous phase fluid dispersed in an immiscible phase carrier fluid (e.g., a fluorocarbon oil, silicone oil, or a hydrocarbon oil) or vice versa. Generally, the droplets are formed by shearing two liquid phases. Shearing may comprise any one of vortexing, shaking, flicking, stirring, pipetting, or any other similar method for mixing solutions. Methods of the invention include combining cells with template particles in a first fluid, adding a second fluid, and shearing or agitating the first and second fluid. Preferably, the first fluid is an aqueous phase fluid, and, in some embodiments, may comprise reagents selected from, for example, buffers, salts, lytic enzymes (e.g. proteinase k) and/or other lytic reagents (e. g. Triton X-100, Tween-20, IGEPAL, or combinations thereof), nucleic acid synthesis reagents e.g. nucleic acid amplification reagents or reverse transcription mix, or combinations thereof.

Methods and systems of the invention use template particles to template the formation of monodisperse droplets and isolate target cells. Template particles according to aspects of the invention may comprise hydrogel, for example, selected from agarose, alginate, a polyethylene glycol (PEG), a polyacrylamide (PAA), acrylate, acrylamide/bisacrylamide copolymer matrix, azide-modified PEG, poly-lysine, polyethyleneimine, and combinations thereof. In certain instances, template particles may be shaped to provide an enhanced affinity for target cells. For example, the template particles may be generally spherical but the shape may contain features such as flat surfaces, craters, grooves, protrusions, and other irregularities in the spherical shape that promote an association with the target cell such that the shape of the template particle increases the probability of templating a droplet that contains the target cell.

In some aspects, methods and systems of the invention provide template particles that include one or more internal compartments. The internal compartments may contain a reagent or compound that is releasable upon an external stimulus. Reagents contained by the template particle may include, for example, cell lysis reagents or nucleic acid synthesis reagents (e.g., a polymerase). The external stimulus may be heat, osmotic pressure, or an enzyme. For example, in some instances, methods of the invention include releasing a reverse transcriptase directly inside of a droplet containing mRNA.

In some aspects, methods and systems of the invention provide a library prep method for analyzing a transcriptome of a single cell. Methods include releasing mRNA from a single target cell contained inside a droplet. In some embodiments, the released mRNA attaches to a poly T sequence of a barcoded capture probe attached to a template particle via complementary base pairing. Alternatively, the released RNA attaches to a gene-specific sequence of the barcoded capture probe. Following attachment of the mRNA molecule with the capture probe, a reverse transcriptase synthetizes cDNA and thereby creates a first strand comprising cDNA and the capture probe sequence. The mRNA molecule first strand hybrid is then denatured using any method known in the art, such as, exposure to a denaturing temperature. In a next step, a second strand primer comprising a random hexamer sequence anneals with the first strand to form a DNA-primer hybrid. A DNA polymerase synthesizes a complementary second strand. In some instances, the second strand is amplified by, for example, PCR, to generate a plurality of amplicons which are analyzed to ascertain an expression profile of the single cell.

In certain aspects, this disclosure provides a kit for single cell profiling according to methods of the invention. The kit includes template particles comprising a plurality of capture sequences specific to one or more genes of interest. A researcher following instructions provided by the kit can use template particles to assay single cell expression of specific genes of interest, such as, oncogenes. The kit can allow for single cell profiling according to methods described throughout this disclosure (e.g., at FIG. 1). Template particles may be custom designed for the user's specific needs, for example, designed to include capture probe sequences specific to the certain genes of interest, such as oncogenes. The template particles may be shipped inside sample preparation tubes, or sample collection tubes, such as, blood collection tubes. The template particles are preferably in a dried format. The kit may further include reagents, such as, cell lysis reagents, and nucleic acid synthesis reagents.

In other aspects, methods and systems of the invention provide a method of collecting data regarding a transcriptome of a single cell. The method comprises the steps of releasing a plurality of distinct mRNA molecules from single cells inside monodisperse droplets and collecting data regarding a transcriptome of the single cells and sending the data to a computer. A computer can be connected to a sequencing apparatus. Data corresponding to the transcriptome can further be stored after sending, for example the data can be stored on a computer-readable medium which can be extracted from the computer. Data can be transmitted from the computer to a remote location, for example, via the internet.

DETAILED DESCRIPTION

This disclosure provides systems and methods of using template particles to form monodisperse droplets for segregating single cells and preparing a library preparation thereof to profile expression of the single cells. The disclosed methods involve the use of template particles to template the formation of monodisperse droplets to generally capture a single target cell in an encapsulation, derive a plurality of distinct RNA from the singe target cell, and prepare a library of nucleic acids that can be traced to the cell from which they were derived, and quantitate distinct RNA to generate an expression profile of the single target cell.

Methods of the invention can be used to prepare libraries for single cell analysis of, for example, at least 100 cells, at least 1000 cells, at least 1,000,000 cells, at least 2,000,000 cells, or more, from a single reaction tube.

Figure 1:
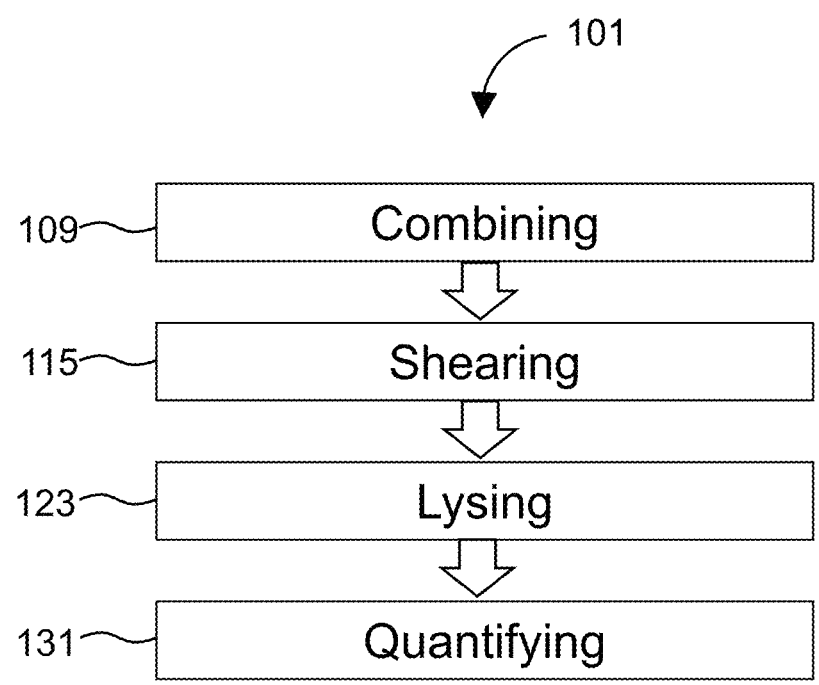
FIG. 1 diagrams a method for single cell profiling.

FIG. 1 diagrams a method 101 for single cell profiling. The method 101 includes combining 109 template particles with target cells in a first fluid, and adding a second fluid that is immiscible with the first fluid to the mixture. The first fluid is preferably an aqueous fluid. While any suitable order may be used, in some instances, a tube may be provided comprising the template particles. The tube can be any type of tube, such as a sample preparation tube sold under the trade name Eppendorf, or a blood collection tube, sold under the trade name Vacutainer. Template particles may be in dried format. Combining 109 may include using a pipette to pipette a sample comprising cells and, for example, the aqueous fluid into the tube containing template particles and then adding a second fluid that is immiscible, such as oil.

The method 101 then includes shearing 115 the fluids to generate monodisperse droplets, i.e., droplets. Preferably, shearing comprises vortexing the tube containing the fluids by pushing the tube onto a vortexer. After vortexing 115, a plurality (e.g., thousands, tens of thousands, hundreds of thousands, one million, two million, ten million, or more) of aqueous partitions is formed essentially simultaneously. Vortexing causes the fluids to partition into a plurality of monodisperse droplets. A substantial portion of droplets will contain a single template particle and a single target cell. Droplets containing more than one or none of a template particle or target cell can be removed, destroyed, or otherwise ignored.

The next step of the method 101 is to lyse 123 the target cells. Cell lysis 123 may be induced by a stimulus, such as, for example, lytic reagents, detergents, or enzymes. Reagents to induce cell lysis may be provided by the template particles via internal compartments. In some embodiments, lysing 123 involves heating the monodisperse droplets to a temperature sufficient to release lytic reagents contained inside the template particles into the monodisperse droplets. This accomplishes cell lysis 123 of the target cells, thereby releasing mRNA inside of the droplets that contained the target cells.

After lysing 123 target cells inside the droplets, mRNA is released and subsequently quantified 131. Quantifying 131 the mRNA generally requires synthesizing cDNA to generate a library comprising cDNA with a barcode sequence to allow each library sequence to be traced back to the single cell from which the mRNA was derived. In preferred embodiments, template particles isolated with the mRNA include a plurality of barcoded capture sequences that hybridize with target mRNA. After hybridization, cDNA is synthesized by reverse transcription. Reagents for reverse transcription can be provided in variety of ways in a variety of formats. In some instances, reagents and reverse transcriptase are provided by the template particles. Once a library is generated comprising barcoded cDNA, the cDNA can be amplified, by for example, PCR, to generate amplicons for sequencing. Sequence reads are processed according to methods described herein to accomplish the quantification of 131 mRNA.

In some aspects, the target cells may include live cells obtained from, for example, a sample (tissue of bodily fluid) of a patient. The sample may include a fine needle aspirate, a biopsy, or a bodily fluid from the patient. Upon being isolated from the sample, the cells may be processed by, for example, generating a single cell suspension with an appropriate solution. Such solution will generally be a balanced salt solution, e.g. normal saline, PBS, Hank's balanced salt solution, etc., and in certain instances supplemented with fetal calf serum or other naturally occurring factors, in conjunction with an acceptable buffer at low concentration, generally from 5-25 mM. Convenient buffers include HEPES (4-(2-hydroxyethyl)-1-piperazineethanesulfonic acid), phosphate buffers, lactate buffers, etc. The separated cells can be collected in any appropriate medium that maintains the viability of the cells, usually having a cushion of serum at the bottom of the collection tube. Various media are commercially available and may be used according to the nature of the cells, including Dulbecco's modified eagle medium (dMEM), Hank's balanced salt solution (HBSS), phosphate buffered saline (PBS), Dulbecco's phosphate buffered saline (dPBS), Roswell Park Memorial Institute medium (RPMI), Iscove's medium, etc., frequently supplemented with fetal calf serum.

Methods and systems of the invention use template particles to template the formation of monodisperse droplets and isolate single target cells. The disclosed template particles and methods for targeted library preparation thereof leverage the particle-templated emulsification technology previously described in, Hatori et. al., Anal. Chem., 2018 (90):9813-9820, which is incorporated by reference. Essentially, micron-scale beads (such as hydrogels) or "template particles" are used to define an isolated fluid volume surrounded by an immiscible partitioning fluid and stabilized by temperature insensitive surfactants.

The template particles of the present disclosure may be prepared using any method known in the art. Generally, the template particles are prepared by combining hydrogel material, e.g., agarose, alginate, a polyethylene glycol (PEG), a polyacrylamide (PAA), Acrylate, Acrylamide/bisacrylamide copolymer matrix, and combinations thereof. Following the formation of the template particles they are sized to the desired diameter. In some embodiments, sizing of the template particles is done by microfluidic co-flow into an immiscible oil phase.

In some embodiments of the template particles, a variation in diameter or largest dimension of the template particles such that at least 50% or more, e.g., 60% or more, 70% or more, 80% or more, 90% or more, 95% or more, or 99% or more of the template particles vary in diameter or largest dimension by less than a factor of 10, e.g., less than a factor of 5, less than a factor of 4, less than a factor of 3, less than a factor of 2, less than a factor of 1.5, less than a factor of 1.4, less than a factor of 1.3, less than a factor of 1.2, less than a factor of 1.1, less than a factor of 1.05, or less than a factor of 1.01.

Template particles may be porous or nonporous. In any suitable embodiment herein, template particles may include microcompartments (also referred to herein as "internal compartment"), which may contain additional components and/or reagents, e.g., additional components and/or reagents that may be releasable into monodisperse droplets as described herein. Template particles may include a polymer, e.g., a hydrogel. Template particles generally range from about 0.1 to about 1000 µm in diameter or largest dimension. In some embodiments, template particles have a diameter or largest dimension of about 1.0 µm to 1000 µm, inclusive, such as 1.0 µm to 750 µm, 1.0 µm to 500 µm, 1.0 µm to 250 µm, 1.0 µm to 200 µm, 1.0 µm to 150 µm 1.0 µm to 100 µm, 1.0 µm to 10 µm, or 1.0 µm to 5 µm, inclusive. In some embodiments, template particles have a diameter or largest dimension of about 10 µm to about 200 µm, e.g., about 10 µm to about 150 µm, about 10 µm to about 125 µm, or about 10 µm to about 100 µm.

In practicing the methods as described herein, the composition and nature of the template particles may vary. For instance, in certain aspects, the template particles may be microgel particles that are micron-scale spheres of gel matrix. In some embodiments, the microgels are composed of a hydrophilic polymer that is soluble in water, including alginate or agarose. In other embodiments, the microgels are composed of a lipophilic microgel.

In other aspects, the template particles may be a hydrogel. In certain embodiments, the hydrogel is selected from naturally derived materials, synthetically derived materials and combinations thereof. Examples of hydrogels include, but are not limited to, collagen, hyaluronan, chitosan, fibrin, gelatin, alginate, agarose, chondroitin sulfate, polyacrylamide, polyethylene glycol (PEG), polyvinyl alcohol (PVA), acrylamide/bisacrylamide copolymer matrix, polyacrylamide/poly(acrylic acid) (PAA), hydroxyethyl methacrylate (HEMA), poly N-isopropylacrylamide (PNIPAM), and polyanhydrides, poly(propylene fumarate) (PPF).

In some embodiments, the presently disclosed template particles further comprise materials which provide the template particles with a positive surface charge, or an increased positive surface charge. Such materials may be without limitation poly-lysine or Polyethyleneimine, or combinations thereof. This may increase the chances of association between the template particle and, for example, a cell which generally have a mostly negatively charged membrane.

Other strategies may be used to increase the chances of templet particle-target cell association, which include creation of specific template particle geometry. For example, in some embodiments, the template particles may have a general spherical shape but the shape may contain features such as flat surfaces, craters, grooves, protrusions, and other irregularities in the spherical shape.

Any one of the above described strategies and methods, or combinations thereof may be used in the practice of the presently disclosed template particles and method for targeted library preparation thereof. Methods for generation of template particles, and template particles-based encapsulations, were described in International Patent Publication WO 2019/139650, which is incorporated herein by reference.

Creating template particle-based encapsulations for single cell expression profiling comprises combining target cells with a plurality of template particles in a first fluid to provide a mixture in a reaction tube. The mixture is then incubated to allow association of the plurality of the template particles with target cells. A portion of the plurality of template particles may become associated with the target cells. The mixture is then combined with a second fluid which is immiscible with the first fluid. The fluid and the mixture are then sheared so that a plurality of monodisperse droplets is generated within the reaction tube. The monodisperse droplets generated comprise (i) at least a portion of the mixture, (ii) a single template particle, and (iii) a single target particle. Of note, in practicing methods of the invention provided by this disclosure a substantial number of the monodisperse droplets generated will comprise a single template particle and a single target particle, however, in some instances, a portion of the monodisperse droplets may comprise none or more than one template particle or target cell.

In some embodiments, to increase the chances of generating an encapsulation, such as, a monodisperse droplet that contains one template particle and one target cell, the template particles and target cells are combined at a ratio wherein there are more template particles than target cells. For example, the ratio of template particles to target cells 213 combined in a mixture as described above may be in a range of 5:1 to 1,000:1, respectively. In other embodiments, the template particles and target cells are combined at a ratio of 10:1, respectively. In other embodiments, the template particles and target cells are combined at a ratio of 100:1, respectively. In other embodiments, the template particles and target cells are combined at a ratio of 1000:1, respectively.

To generate a monodisperse emulsion, the presently disclosed method includes a step of shearing the second mixture provided by combining a first mixture comprising target particles and target cells with a second fluid immiscible with the first mixture. Any suitable method or technique may be utilized to apply a sufficient shear force to the second mixture. For example, the second mixture may be sheared by flowing the second mixture through a pipette tip. Other methods include, but are not limited to, shaking the second mixture with a homogenizer (e.g., vortexer), or shaking the second mixture with a bead beater. In some embodiments, vortex may be performed for example for 30 seconds, or in the range of 30 seconds to 5 minutes. The application of a sufficient shear force breaks the second mixture into monodisperse droplets that encapsulate one of a plurality of template particles.

In some aspects, generating the template particles-based monodisperse droplets involves shearing two liquid phases. The mixture is the aqueous phase and, in some embodiments, comprises reagents selected from, for example, buffers, salts, lytic enzymes (e.g. proteinase k) and/or other lytic reagents (e. g. Triton X-100, Tween-20, IGEPAL, bm 135, or combinations thereof), nucleic acid synthesis reagents e.g. nucleic acid amplification reagents or reverse transcription mix, or combinations thereof. The fluid is the continuous phase and may be an immiscible oil such as fluorocarbon oil, a silicone oil, or a hydrocarbon oil, or a combination thereof. In some embodiments, the fluid may comprise reagents such as surfactants (e.g. octylphenol ethoxylate and/or octylphenoxypolyethoxyethanol), reducing agents (e.g. DTT, beta mercaptoethanol, or combinations thereof).

In practicing the methods as described herein, the composition and nature of the monodisperse droplets, e.g., single-emulsion and multiple-emulsion droplets, may vary. As mentioned above, in certain aspects, a surfactant may be used to stabilize the droplets. The monodisperse droplets described herein may be prepared as emulsions, e.g., as an aqueous phase fluid dispersed in an immiscible phase carrier fluid (e.g., a fluorocarbon oil, silicone oil, or a hydrocarbon oil) or vice versa. Accordingly, a droplet may involve a surfactant stabilized emulsion, e.g., a surfactant stabilized single emulsion or a surfactant stabilized double emulsion. Any convenient surfactant that allows for the desired reactions to be performed in the droplets may be used. In other aspects, monodisperse droplets are not stabilized by surfactants.

Figure 2:
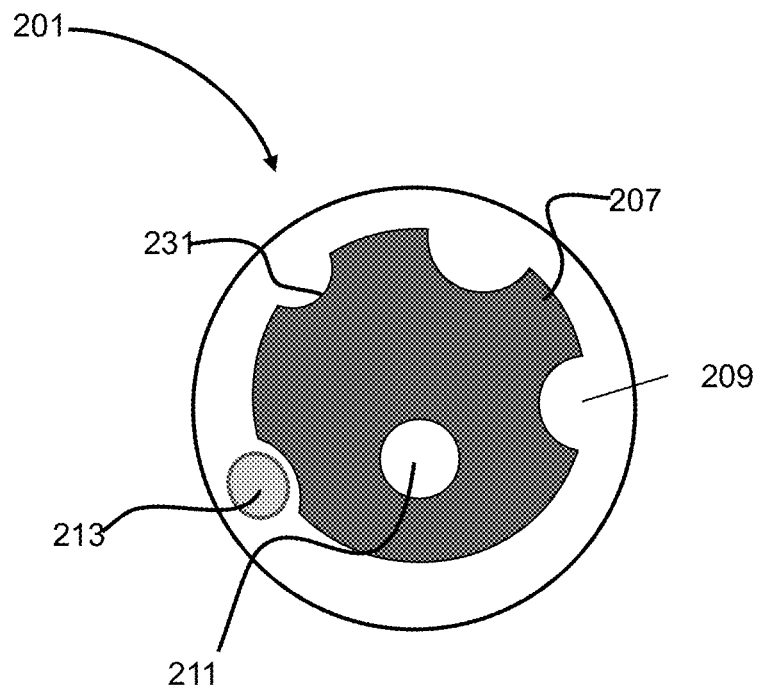
FIG. 2 illustrates a droplet according to one aspect of the invention.

FIG. 2 illustrates a droplet 201 according to one aspect of the invention. The depicted droplet 201 is a single one of a plurality of monodisperse droplets generated by shearing a mixture according to methods of the invention. The droplet 201 comprises a template particle 207 and a single target cell 213. The template particle 207 illustrated comprises crater-like depressions 231 to facilitate capture of single cells 213. The template particle 231 further comprises an internal compartment 211 to deliver one or more reagents into the droplet 201 upon stimulus.

In some embodiments, the template particles contain multiple internal compartments. The internal compartments of the template particles may be used to encapsulate reagents that can be triggered to release a desired compound, e.g., a substrate for an enzymatic reaction, or induce a certain result, e.g. lysis of an associated target cell. Reagents encapsulated in the template particles' compartment may be without limitation reagents selected from buffers, salts, lytic enzymes (e.g. proteinase k), other lytic reagents (e. g. Triton X-100, Tween-20, IGEPAL, bm 135), nucleic acid synthesis reagents, or combinations thereof.

Lysis of single target cells occurs within the monodisperse droplets and may be induced by a stimulus such as heat, osmotic pressure, lytic reagents (e.g., DTT, beta-mercaptoethanol), detergents (e.g., SDS, Triton X-100, Tween-20), enzymes (e.g., proteinase K), or combinations thereof. In some embodiments, one or more of the said reagents (e.g., lytic reagents, detergents, enzymes) is compartmentalized within the template particle. In other embodiments, one or more of the said reagents is present in the mixture. In some other embodiments, one or more of the said reagents is added to the solution comprising the monodisperse droplets, as desired.

Figure 3:
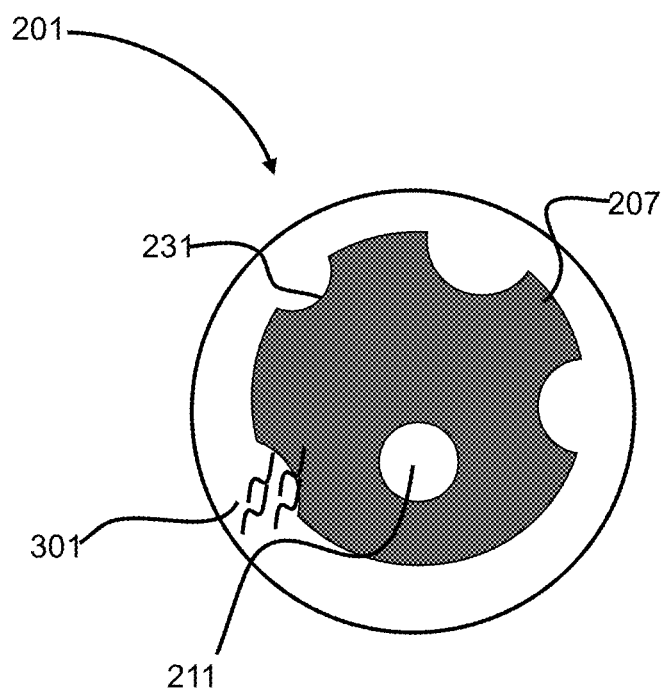
FIG. 3 illustrates a droplet following lysis of a target cell.

FIG. 3 illustrates a droplet 201 following lysis of a target cell. The depicted droplet 201 comprises a template particle 207 and released mRNA 301. Methods of the invention quantify amplified products of the released mRNAs 301, preferably by sequencing.

In preferred embodiments, template particles comprise a plurality of capture probes. Generally, the capture probe of the present disclosure is an oligonucleotide. In some embodiments, the capture probes are attached to the template particle's material, e.g. hydrogel material, via covalent acrylic linkages. In some embodiments, the capture probes are acrydite-modified on their 5' end (linker region). Generally, acrydite-modified oligonucleotides can be incorporated, stoichiometrically, into hydrogels such as polyacrylamide, using standard free radical polymerization chemistry, where the double bond in the acrydite group reacts with other activated double bond containing compounds such as acrylamide. Specifically, copolymerization of the acryditemodified capture probes with acrylamide including a crosslinker, e.g. N,N'-methylenebis, will result in a crosslinked gel material comprising covalently attached capture probes. In some other embodiments, the capture probes comprise Acrylate terminated hydrocarbon linker and combining the said capture probes with a template particle will cause their attachment to the template particle.

Figure 4:
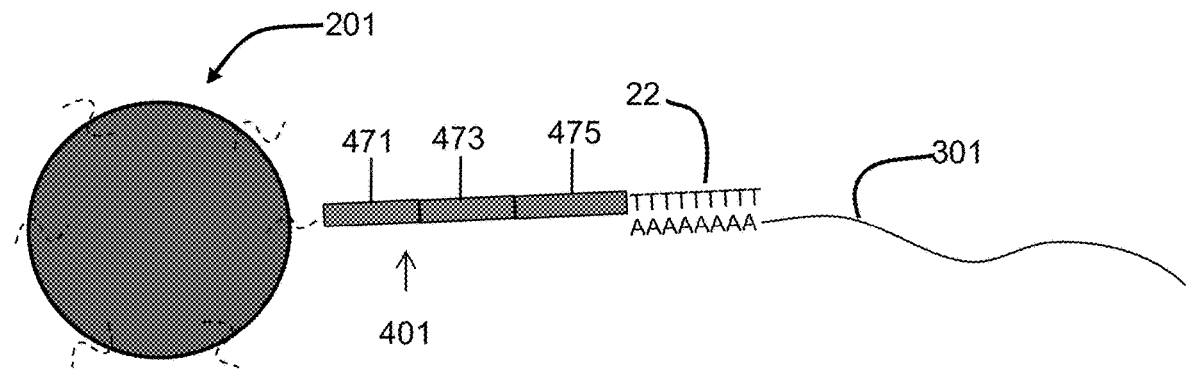
FIG. 4 illustrates the capture of mRNA.
Figure 5:
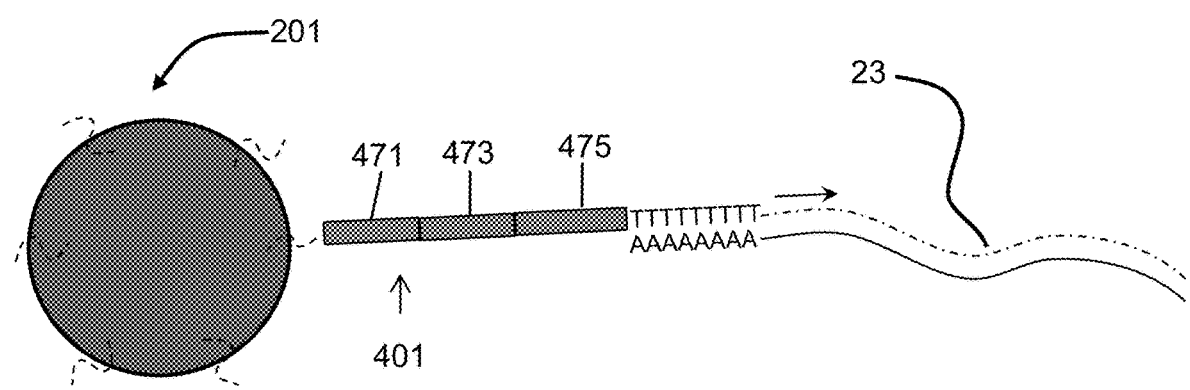
FIG. 5 illustrates synthesis of cDNA to form a first strand.
Figure 6:
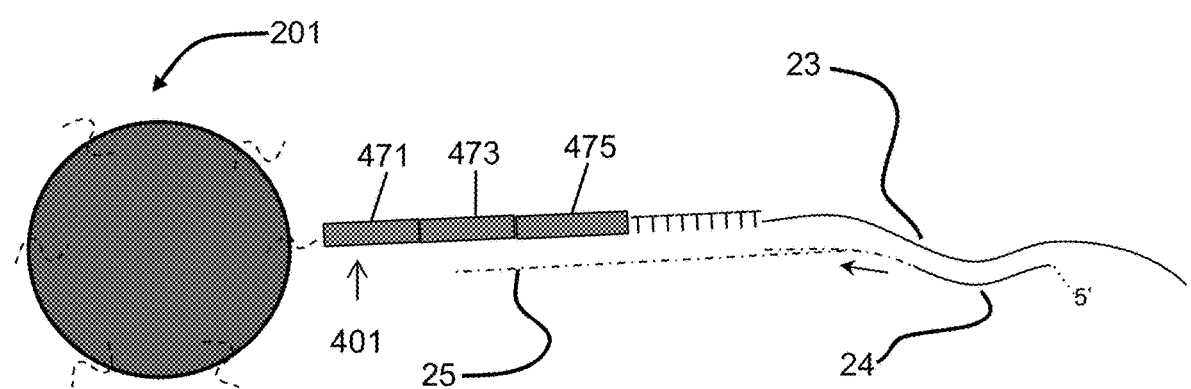
FIG. 6 illustrates amplification of a first strand to generate an amplicon.

FIGS. 4-6 show an exemplary method for nonspecific amplification of mRNA according to certain aspects of the disclosure. In particular, the method relies on the presence of a poly A tail at the 3' end of a mRNA for the non-specific capture of mRNAs.

FIG. 4 illustrates the capture of mRNA 301. Shown, is a template particle 201 comprising a plurality of capture probes 401 illustrated schematically by curved broken lines. One of the capture probes 401 is featured in a larger scale and in detail. The capture probe 401 preferably comprises, from 5' end to 3' end, a linker region to allow covalent bond with the template particle 201, a PR1 471 nucleotide sequence region comprising a universal primer nucleotide sequence, at least one barcode region B1 473, which may include an index 475 nucleotide sequence index, and/or a UMI, the capture probe 201 further including a capture nucleotide sequence 22 comprising a poly T nucleotide sequence. A released nucleic acid, i.e., mRNA molecule 301 comprising a poly A sequence attaches to the capture probe's poly T sequence 22 via complementary base pairing. Following the hybridization of the mRNA molecule 301 and the capture probe 401, a reverse transcriptase is used to perform a reverse transcription reaction to synthetize cDNA and thereby create a first strand comprising the cDNA and the capture probe sequence.

FIG. 5 illustrates synthesis of cDNA to form a first strand 23. A reverse transcriptase (not shown) synthesizes cDNA from mRNA that is hybridized to a poly T sequence of a capture probe 401. After synthesis, a first strand 23 is formed, wherein the first strand 23 comprises the cDNA and the capture probe 401 sequence. Following synthesis, the mRNA molecule 301-first strand 23 hybrid may be denatured (not shown) using any method traditional in the art, such as an exposure to a denaturing temperature.

FIG. 6 illustrates amplification of a first strand to generate an amplicon. In particular, following the formation of a first strand 23, a second strand primer 24 comprising a random sequence, such as, a random hexamer, anneals with the first strand 23 to form a DNA-primer hybrid. A DNA polymerase is used to synthesize a complementary second strand 25, i.e., an amplicon. In the embodiment illustrated, the second strand primer 24 comprises a "tail" region which does not hybridize with the first strand 23. In some embodiments, the tail region comprises a second universal primer sequence. The second strand 25 may be further amplified by PCR to generate a plurality of amplicons, and quantified by DNA sequencing.

Amplification or nucleic acid synthesis, as used herein, generally refers to methods for creating copies of nucleic acids by using thermal cycling to expose reactants to repeated cycles of heating and cooling, and to permit different temperature-dependent reactions (e.g. by polymerase chain reaction (PCR). Any suitable PCR method known in the art may be used in connection with the presently described methods. Non limiting examples of PCR reactions include real-time PCR, nested PCR, multiplex PCR, quantitative PCR, TS-PCR, or touchdown PCR.

The terms "nucleic acid amplification reagents" or "reverse transcription mix" encompass without limitation dNTPs (mix of the nucleotides dATP, dCTP, dGTP and dTTP), buffer/s, detergent/s, or solvent/s, as required, and suitable enzyme such as polymerase or reverse transcriptase. The polymerase used in the presently disclosed targeted library preparation method may be a DNA polymerase, and may be selected from, but is not limited to, Taq DNA polymerase, Phusion polymerase, or Q5 polymerase. The reverse transcriptase used in the presently disclosed targeted library preparation method may be for example, Moloney murine leukemia virus (MMLV) reverse transcriptase, or maxima reverse transcriptase. In some embodiments, the general parameters of the reverse transcription reaction comprise an incubation of about 15 minutes at 25 degrees and a subsequent incubation of about 90 minutes at 52 degrees. Nucleic acid amplification reagents are commercially available, and may be purchased from, for example, New England Biolabs, Ipswich, Mass., USA, or Clonetech.

Figure 7:
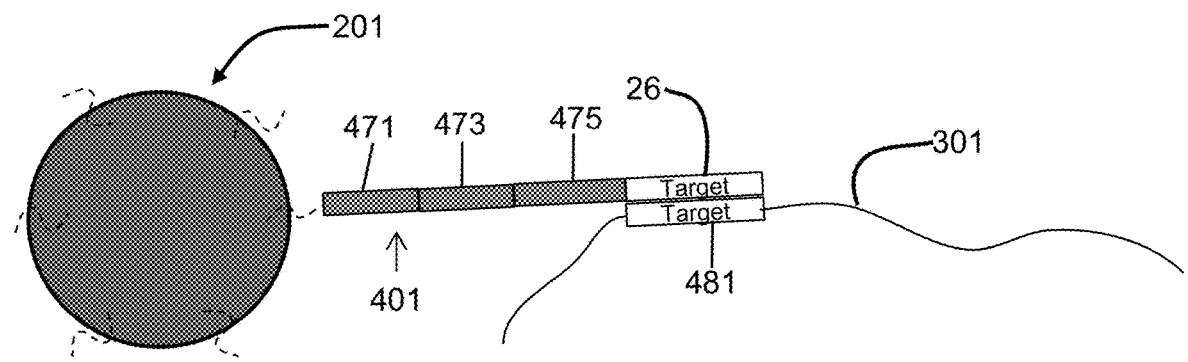
FIG. 7 illustrates a method for sequence-specific capture of mRNA.
Figure 8:
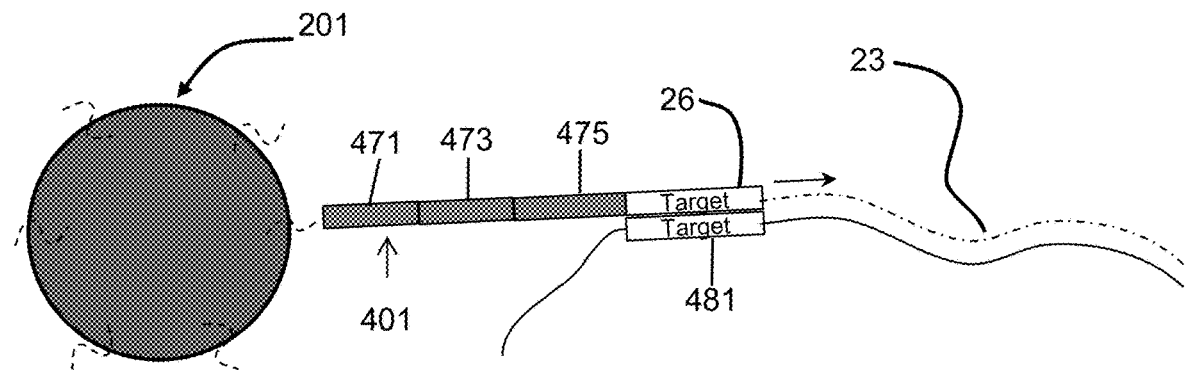
FIG. 8 illustrates synthesis of cDNA to form a first strand.
Figure 9:
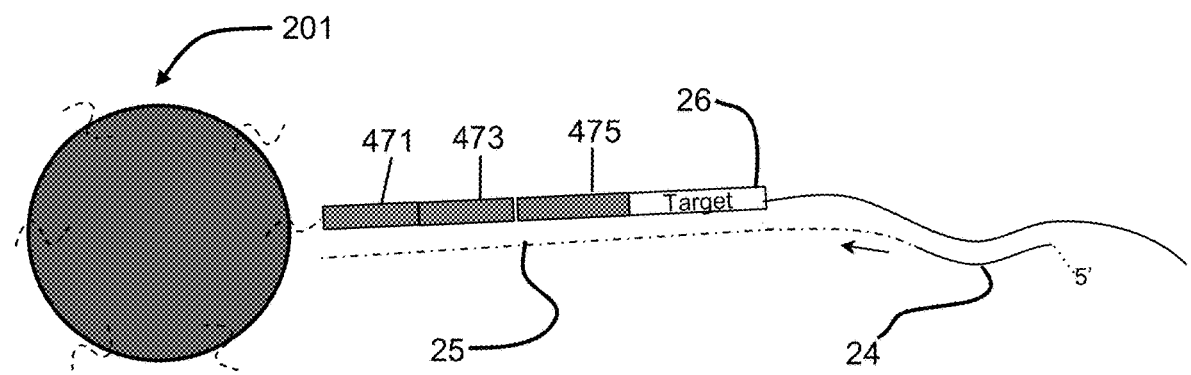
FIG. 9 illustrates amplification of a first strand to generate an amplicon.

FIGS. 7-9 illustrate a method for sequence-specific amplification of mRNA according to certain aspects of the disclosure.

FIG. 7 illustrates a method for sequence-specific capture of mRNA 301. The template particle 201 comprises a plurality of capture probes 401 illustrated schematically by curved broken lines. A featured capture probe 401 comprises, from 5' end to 3' end, a linker region to allow covalent bond with the template particle 201, a PR1" region comprising a universal primer nucleotide sequence, at least one barcode region B1, which may include an index sequence, and/or a UMI, the capture probe 401 further comprising and a capture sequence comprising a gene-specific sequence 26.

A molecule of mRNA 301, released inside a monodisperse droplet, comprising a target sequence 481 complementary to the gene-specific sequence 26 attaches to the capture probe's gene-specific sequence 26 via complementary base pairing. The gene-specific sequence may comprise any sequence of interest, for example, a sequence corresponding to an oncogene.

For example, in some instances template particles 201 according to aspects of the invention may comprise capture probes with certain sequences specific to genes of interest, such as, oncogenes. Some non-limiting examples of genes of interest that may be assayed for include, but are not limited to, BAX, BCL2L1, CASP8, CDK4, ELK1, ETS1, HGF, JAK2, JUNB, JUND, KIT, KITLG, MCL1, MET, MOS, MYB, NFKBIA, EGFR, Myc, EpCAM, NRAS, PIK3CA, PML, PRKCA, RAF1, RARA, REL, ROS1, RUNX1, SRC, STAT3, CD45, cytokeratins, CEA, CD133, HER2, CD44, CD49f, CD146, MUC1/2, ABL1, AKT1, APC, ATM, BRAF, CDH1, CDKN2A, CTNNB1, EGFR, ERBB2, ERBB4, EZH2, FBXW7, FGFR2, FGFR3, FLT3, GNAS, GNAQ, GNA11, HNF1A, HRAS, IDH1, IDH2, JAK2, JAK3, KDR, KIT, KRAS, MET, MLH1, NOTCH1, NPM1, NRAS, PDGFRA, PIK3CA, PTEN, PTPN11, RB1, RET, SMAD4, STK11, TP53, VHL, and ZHX2.

FIG. 8 illustrates the synthesis of cDNA to form a first strand 23. A reverse transcriptase (not shown) synthesizes cDNA from mRNA that is hybridized to gene-specific sequence of a capture probe 12. Following the hybridization of the target mRNA molecule 301 and the capture probe 12, a reverse transcription reaction is performed to synthetize a cDNA and create a first strand 23. The first strand 23 comprises synthesized cDNA and the capture probe 401 sequence. The target mRNA molecule-first strand hybrid is than denatured using methods traditional in the art (not shown), and second strand primer 24 comprising a random hexamer sequence anneals with complementary sequence of the first strand 23 to form a DNA-primer hybrid.

FIG. 9 illustrates amplification of a first strand 23 to generate an amplicon 25. In particular, following the formation of a first strand 23, a second strand primer 24 comprising a random sequence, such as, a random hexamer, anneals with the first strand 23 to form a DNA-primer hybrid. A DNA polymerase is used to synthesize a complementary second strand 25, i.e., an amplicon 25. In the embodiment illustrated, the second strand primer 24 comprises a "tail" region which does not hybridize with the first strand 23. In some embodiments, the tail region comprises a second universal primer sequence.

According to aspects of the present disclosure, the term "universal primer sequence" generally refers to a primer binding site, e.g., a primer sequence that would be expected to hybridize (base-pair) to, and prime, one or more loci of complementary sequence, if present, on any nucleic acid fragment. In some embodiments, the universal primer sequences used with respect to the present methods are P5 and P7.

The term barcode region may comprise any number of barcodes, index or index sequence, UMIs, which are unique, i.e., distinguishable from other barcode, or index, UMI sequences. The sequences may be of any suitable length which is sufficient to distinguish the barcode, or index, sequence from other barcode sequences. A barcode, or index, sequence may have a length of 4, 5, 6, 7, 8, 9, 10, 11, 12, 13, 14, 15, 16, 17, 18, 19, 20, 21, 22, 23, 24, 25 nucleotides, or more. In some embodiments, the barcodes, or indices, are pre-defined and selected at random.

In some methods of the invention, a barcode sequence may comprise unique molecule identifiers (UMIs). UMIs are a type of barcode that may be provided to a sample to make each nucleic acid molecule, together with its barcode, unique, or nearly unique. This may be accomplished by adding one or more UMIs to one or more capture probes of the present invention. By selecting an appropriate number of UMIs, every nucleic acid molecule in the sample, together with its UMI, will be unique or nearly unique.

UMIs are advantageous in that they can be used to correct for errors created during amplification, such as amplification bias or incorrect base pairing during amplification. For example, when using UMIs, because every nucleic acid molecule in a sample together with its UMI or UMIs is unique or nearly unique, after amplification and sequencing, molecules with identical sequences may be considered to refer to the same starting nucleic acid molecule, thereby reducing amplification bias. Methods for error correction using UMIs are described in Karlsson et al., 2016, Counting Molecules in cell-free DNA and single cells RNA", Karolinska Institutet, Stockholm Sweden, incorporated herein by reference.

In certain aspects, methods of the invention include combining template particles with target cells in a first fluid, adding a second fluid to the first fluid, shearing the fluids to generate a plurality of monodisperse droplets simultaneously that contain a single one of the template particles and a single one of the target cells, in which the template particles preferably include one or more oligos useful in template switching oligo (TSO) embodiments. The method preferably also includes lysing each of the single target cells contained within the monodisperse droplets to release a plurality of distinct mRNA molecules; and quantifying the plurality of distinct mRNA molecules by, for example, using template switching PCR (TS-PCR), as discussed in U.S. Pat. No. 5,962,272, which is incorporated herein by reference. TS-PCR is a method of reverse transcription and polymerase chain reaction (PCR) amplification that relies on a natural PCR primer sequence at the polyadenylation site, also known as the poly(A) tail, and adds a second primer through the activity of murine leukemia virus reverse transcriptase. This method permits reading full cDNA sequences and can deliver high yield from single sources, even single cells that contain 10 to 30 picograms of mRNA.

TS-PCR generally relies on the intrinsic properties of Moloney murine leukemia virus (MMLV) reverse transcriptase and the use of a unique TSO. During first-strand synthesis, upon reaching the 5' end of the mRNA template, the terminal transferase activity of the MMLV reverse transcriptase adds a few additional nucleotides (mostly deoxycytidine) to the 3' end of the newly synthesized cDNA strand. These bases may function as a TSO-anchoring site. After base pairing between the TSO and the appended deoxycytidine stretch, the reverse transcriptase "switches" template strands, from cellular RNA to the TSO, and continues replication to the 5' end of the TSO. By doing so, the resulting cDNA contains the complete 5' end of the transcript, and universal sequences of choice are added to the reverse transcription product. This approach makes it possible to efficiently amplify the entire full-length transcript pool in a completely sequence-independent manner.

Figure 10:
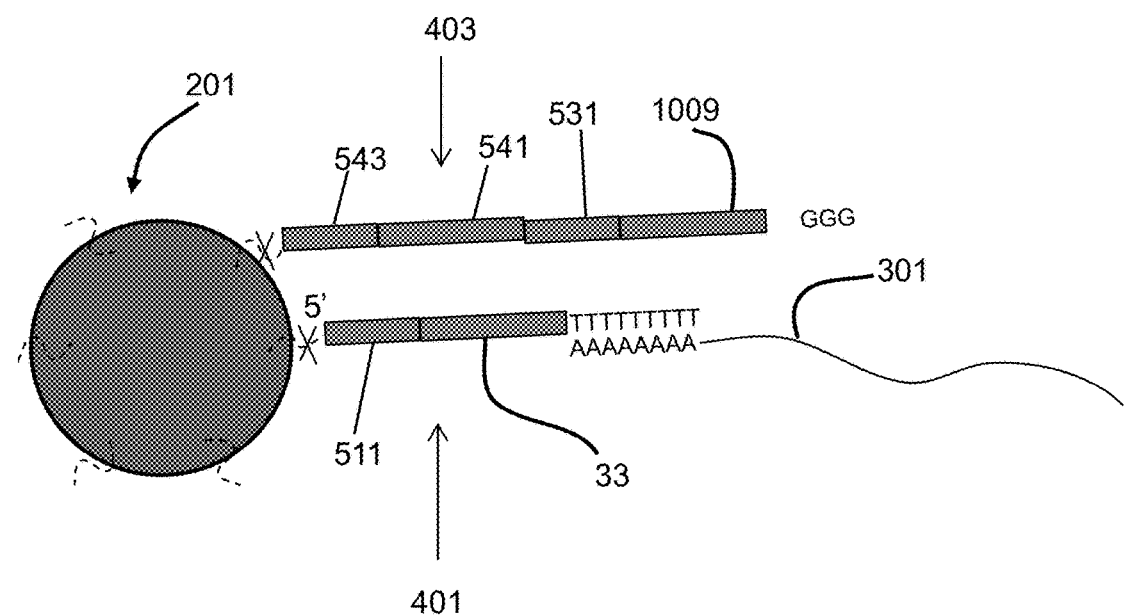
FIG. 10 illustrates the capture of mRNA according to TSO embodiments.

FIG. 10 illustrates the capture of mRNA 301 according to TSO embodiments. The TSO 1009 is an oligo that hybridizes to untemplated C nucleotides added by the reverse transcriptase during reverse transcription. The TSO may add, for example, a common 5' sequence to full length cDNA that is used for downstream cDNA amplification.

Shown, is a template particle 201 that comprises a first capture probe 401, and a second capture probe 403. The first capture probe 401 preferably comprises, from 5' end to 3' end, a linker region to allow a covalent bond with the template particle 201, a P5 511 nucleotide sequence region comprising a universal primer nucleotide sequence, at least one barcode 33, and a capture nucleotide sequence 22 comprising a poly T nucleotide sequence. The second capture probe 403 preferably includes a TSO 1009, a UMI 531, a second barcode 541, a P7 543 nucleotide sequence region comprising a universal primer nucleotide sequence. A released nucleic acid, i.e., mRNA molecule 301 comprising a poly A sequence attaches to the first capture probe's 401 poly T sequence 22 via complementary base pairing. Following the hybridization of the mRNA molecule 301 and the capture probe 401, TS-PCR is performed using a reverse transcriptase, i.e., murine leukemia virus reverse transcriptase, to synthetize cDNA and thereby create a first strand. During TS-PCR amplification, upon reaching the 5' end of the mRNA template, the terminal transferase activity of the reverse transcriptase adds a few additional nucleotides (mostly deoxycytidine), to the 3' end of the nascent first strand.

Figure 11:
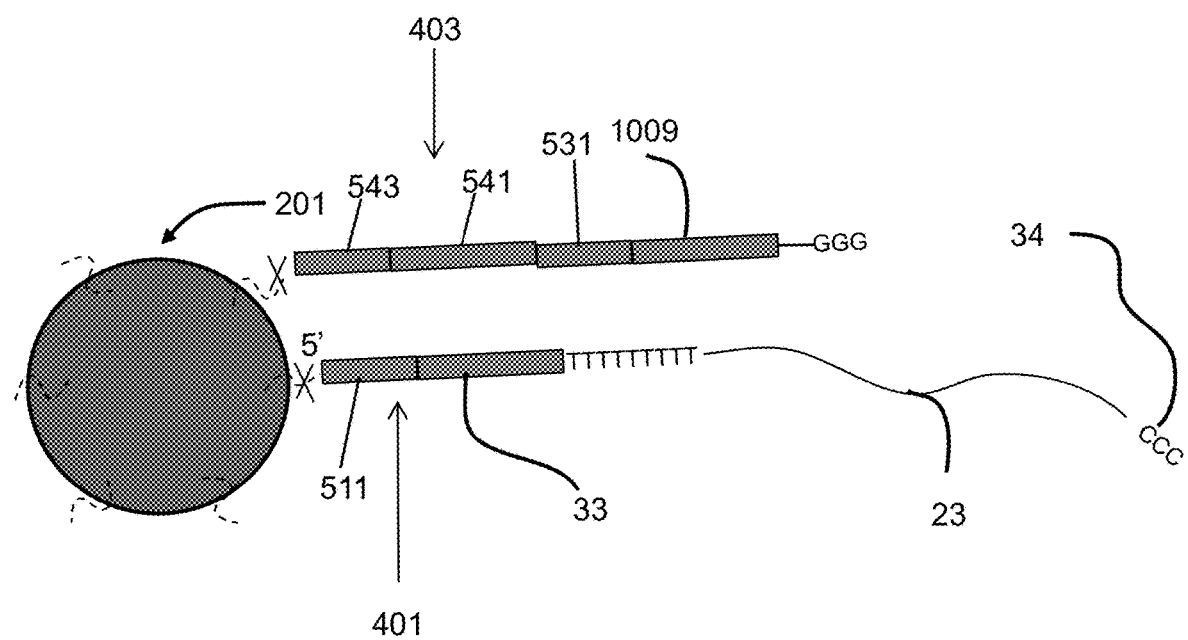
FIG. 11 shows a first strand following TS-PCR amplification.

FIG. 11 shows a first strand 23 following TS-PCR amplification. The first strand 23 includes additional nucleotides that may function as a TSO-anchoring site 34. The TSO-anchoring site 34 may hybridize with the TSO 1009, after base pairing between the TSO and the TSO-anchoring site 34, the reverse transcriptase "switches" template strands, from cellular RNA to the TSO, and continues replication to the 5' end of the TSO. By doing so, the resulting cDNA contains the complete 5' end of the transcript, and sequences from the second capture probe 403. after synthesis of the first strand 23, the first strand 23 including capture probes 401, 403, may be released either by cleaving covalent bonds attaching the capture probes 401, 403 to a surface of the template particle 201, or by dissolving the template particle 201, for example, by heat.

A person with ordinary skills in the art will appreciate that any one of the template particle embodiments, capture probes, primer probes, second strand primers, universal amplification primers, barcodes, UMIs, TSOs, and methods thereof described in any one of the embodiments of the presently disclosed targeted library preparation method may be used in a different combination, or embodiment, of the present method. For example, any one of the presently described second strand primers, or primer probe, may be used to prime any one of the presently disclosed first strand to allow for a DNA synthesis reaction to generate an amplicon.

In preferred embodiments, quantifying released mRNA comprises sequencing, which may be performed by methods known in the art. For example, see, generally, Quail, et al., 2012, A tale of three next generation sequencing platforms: comparison of Ion Torrent, Pacific Biosciences and Illumina MiSeq sequencers, BMC Genomics 13:341. Nucleic acid sequencing techniques include classic dideoxy sequencing reactions (Sanger method) using labeled terminators or primers and gel separation in slab or capillary, or preferably, next generation sequencing methods. For example, sequencing may be performed according to technologies described in U.S. Pub. 2011/0009278, U.S. Pub. 2007/0114362, U.S. Pub. 2006/0024681, U.S. Pub. 2006/0292611, U.S. Pat. Nos. 7,960,120, 7,835,871, 7,232,656, 7,598,035, 6,306,597, 6,210,891, 6,828,100, 6,833,246, and 6,911,345, each incorporated by reference.

The conventional pipeline for processing sequencing data includes generating FASTQ-format files that contain reads sequenced from a next generation sequencing platform, aligning these reads to an annotated reference genome, and quantifying expression of genes. These steps are routinely performed using known computer algorithms, which a person skilled in the art will recognize can be used for executing steps of the present invention. For example, see Kukurba, Cold Spring Harb Protoc, 2015 (11):951-969, incorporated by reference.

After obtaining expression profiles from single cells, the expression profiles can be analyzed by, for example, comparing the profiles with reference or control profiles to ascertain information about the single target cells. For example, see generally, Efroni, Genome Biology, 2015; and Stahlberg, Nucleic Acids Research, 2011, 39(4)e24, each of which incorporated by reference.

In one aspect, methods and systems of the invention provide a method for identifying a rare cell from a heterogeneous cell population. The method includes isolating a plurality of single target cells from the heterogeneous cell population by combining the heterogeneous cells with a plurality of template particles in a first fluid, adding a second fluid that is immiscible with the first fluid, and shearing the fluids to generate an emulsion comprising monodisperse droplets that each contain a single target cell and a single template particle. Methods further include releasing a plurality of mRNA molecules from each of the single target cells contained within the monodisperse droplets and quantifying the plurality of mRNA molecules. Quantifying may include generating a plurality of amplicons of the mRNA molecules wherein each of the amplicons comprise a barcode or index sequence that is unique to the cell from which the mRNA molecule was derived. In some instances, methods may include sequencing the plurality of barcoded amplicons by, for example, next-generation sequencing methods to generate sequence reads for each of the amplicons. Methods may further include processing the sequence reads associated with single cells of the heterogeneous cell population to generate expression profiles for each of the single cells and using the data by, for example, performing a gene clustering analysis to identify one or more cell types or cell states.

In another aspect, methods and systems of the disclosure provide a method for analyzing a heterogeneous tumor biopsy taken from a subject. The method includes obtaining a biopsy from a patient and isolating a population of cells from the biopsy. The method further includes segregating the population of cells into taken from the biopsy into droplets by combining the population of cells with a plurality of template particles in a first fluid, adding a second fluid that is immiscible with the first fluid, and shearing the fluids to generate an emulsion comprising monodisperse droplets that each contain a single one of the population of cells and a single template particle. Methods further include releasing a plurality of mRNA molecules from each one of the segregated single cells contained within the monodisperse droplets and performing transcriptome analysis on one or more genes of the single cells and using the transcriptome data to identify one or more characteristics of the tumor. A characteristic identified can be the presence, or absence, of one or more gene transcripts associated with a cancer. A method disclosed herein can further comprise the step of using the characteristic to diagnose a subject with cancer or a cancer stage or to devise a treatment plan.

In some aspects, methods and systems of the invention provide a method for determining the potential effectiveness of a therapeutic agent. The method comprises segregating a first population of diseased cells into monodisperse droplets with template particles and determining the expression level of at least one nucleic acid from at least one of the diseased cells, thereby producing a disease-state expression signature. The method further includes exposing a second population of disease state cells to an agent and determining the expression level of at least one nucleic acid from at least one of the individual cells from the second population and comparing the expression level from the individual cell from the second population to the disease-state expression signature to thereby determine the effectiveness of the agent against the disease. In some embodiments, the therapeutic agent may be delivered to second population of cells inside monodisperse droplets. For example, the agent may be associated with the template particle by tethering the agent to an external surface of the template particle, or packaging the agent inside a compartment of the template particle such that the agent can be delivered to the cells contained inside the monodisperse droplets.

In any one of the embodiments of the presently disclosed targeted library preparation method, the template particle further comprises a capture moiety. In some embodiments, the capture moiety acts to capture specific target particles, for example, specific types of cells. In some embodiments, the capture moiety comprises an Acrylate-terminated hydrocarbon linker with biotin termination. In some embodiments, the capture moiety is attached to a target-specific capture element. In some embodiments, the target-specific capture element is selected from aptamers and antibodies. Embodiments of the capture moiety and methods thereof are disclosed in world application WO2020069298A1, incorporated herein by reference.

What is claimed is:

1. A method for single cell analysis, the method comprising:
    combining template particles with target cells in a first fluid, wherein each template particle is bound to first capture probes comprising capture sequences and second capture probes comprising template-switching oligos (TSOs);
    adding a second fluid to the first fluid;
    shearing the fluids to generate a plurality of monodisperse droplets simultaneously that contain a single one of the template particles and a single one of the target cells;
    lysing each of the single target cells contained within the monodisperse droplets to release a plurality of distinct mRNA molecules;
    capturing the plurality of distinct mRNA molecules with the first capture probes;
    extending the first capture probes with reverse transcriptase to form nascent first strand cDNAs;
    annealing the nascent first strand cDNAs to the TSOs and copying the TSOs to generate cDNAs that are bound to the template particles and contain copies of the plurality of distinct mRNA molecules and the TSOs; and
    analyzing the cDNAs to quantify the plurality of distinct mRNA molecules.

2. The method of claim 1, further comprising generating an expression profile for each of the single target cells after quantifying the plurality of distinct mRNA molecules.

3. The method of claim 1, wherein shearing the fluids comprises one of using a vortexer or pipetting.

4. The method of claim 3, wherein the template particles comprise features that facilitate capture of the single cells and one or more encapsulated internal compartments that contain reagents.

5. The method of claim 4, wherein the one or more encapsulated internal compartments contain a reagent selected from a group comprising a lytic reagent, a nucleic acid synthesis reagent, or combination thereof.

6. The method of claim 5, wherein the nucleic acid synthesis reagent comprises a polymerase.

7. The method of claim 4, wherein the features that capture the single cells include flat surfaces, craters, or grooves.

8. The method of claim 1, wherein the first of capture probes are oligonucleotides, each comprising:
    a 5' terminal acrydite group;
    a universal primer sequence;
    at least one barcode; and
    one of the capture sequences.

9. The method of claim 8, wherein the capture sequence is selected from one of a poly T nucleotide sequence, a gene-specific nucleotide sequence, or a random nucleotide sequence.

10. The method of claim 1, wherein each of the plurality of distinct mRNA molecules attaches to the template particle by hybridizing to a poly T nucleotide sequence upon release from the single target cells.

11. The method of claim 10, further comprising releasing the cDNAs from the template particles and amplifying the cDNAs by PCR to generate amplicons.

12. The method of claim 10, wherein the mRNA attached to the template particle is reverse transcribed using the TSOs to add a common 5' sequence to the cDNAs.

13. The method of claim 11, wherein quantifying the plurality of distinct mRNA molecules comprises sequencing the amplicons.

14. The method of claim 11, wherein at least one of the target cells 1s a cancer cell.

15. A kit for single cell profiling, the kit comprising:
    a tube containing template particles, wherein each template particle is bound to first capture probes comprising capture sequences and second capture probes comprising template switching oligos (TSOs), features that facilitate capture of single cells onto a surface of the template particle, and one or more encapsulated internal compartment containing a reagent.

16. The kit of claim 15, wherein the reagent is reverse transcriptase.

17. The kit of claim 15, wherein the features that facilitate capture include craters or flat surfaces on generally spherical surfaces of the template particles.

* * * * *